(12) United States Patent
Blaustein

(10) Patent No.: US 11,448,587 B1
(45) Date of Patent: Sep. 20, 2022

(54) METHODS AND APPARATUS FOR DETECTING INCAPACITATING DRUGS

(71) Applicant: Mai Blaustein, Harrison, NY (US)

(72) Inventor: Mai Blaustein, Harrison, NY (US)

(*) Notice: Subject to any disclaimer, the term of this patent is extended or adjusted under 35 U.S.C. 154(b) by 0 days.

(21) Appl. No.: 17/523,306

(22) Filed: Nov. 10, 2021

(51) Int. Cl.
*G01N 21/25* (2006.01)
*G01N 33/94* (2006.01)

(52) U.S. Cl.
CPC .......... *G01N 21/255* (2013.01); *G01N 33/94* (2013.01)

(58) Field of Classification Search
None
See application file for complete search history.

(56) References Cited

U.S. PATENT DOCUMENTS

| | | | | |
|---|---|---|---|---|
| 4,752,689 | A * | 6/1988 | Satake | G01N 21/4738 250/339.07 |
| 9,029,098 | B1 * | 5/2015 | Holcombe | G01N 33/94 435/25 |
| 2004/0162470 | A1 * | 8/2004 | Tu | A61B 5/14532 600/316 |
| 2007/0065338 | A1 * | 3/2007 | Schindler | G01N 21/8483 422/400 |
| 2011/0195507 | A1 * | 8/2011 | Dancer | G01N 21/78 436/24 |
| 2012/0070901 | A1 * | 3/2012 | Bradley | G01N 31/223 436/24 |
| 2013/0209325 | A1 * | 8/2013 | Harooni | G01N 21/78 422/400 |
| 2016/0146726 | A1 * | 5/2016 | Aggarwal | G01N 21/31 250/226 |
| 2017/0079574 | A1 * | 3/2017 | Rodriguez Restrepo | A61B 5/681 |
| 2021/0350897 | A1 * | 11/2021 | Shelton, IV | A61M 15/0066 |

OTHER PUBLICATIONS

"Report on the Analysis of Common Beverages Spike with Gamma-hydroxybutyric Acid (GHB) and Gamma-butyrolactone (GBL) using NMR and the PURGE Solvent-Suppression Technique", C. Lesar, J. Decatur, E. Lukasiewicz, E. Champeil, Feb. 2011.
"Identification of the Date-Rape Drug GHB and its Precursor GBL by Raman Spectroscopy", V. Brewster, H. Edwards, M. Hargreaves and T. Munshi, Sep. 2008.
"A Colorimetric Sensor Array for Detection of the Date-Rape Drug y-Hydroxbutyric Acid (Ghb): A Supramolecular Approach", L. Baumes, M. Buaki Sogo, P. Montes-Navajas, A. Corma and H. Garcia, 2010.
"A Sensor for a Date-Rape Drug, Incorporated Into a Beverage Container", J. Morang, Apr. 2012.
"GHB Free Acid: 11. Isolation and Spectroscopic Characterization for Forensic Analysis", M. Witkowski, L. Ciolino, J. DeFrancesco, Mar. 2006.
"Development of a Method for the Detection of GHB and Other Drugs Using a Handheld Raman Spectroscopy Device", L. O'Connor, May 2014.

(Continued)

*Primary Examiner* — Shawn Decenzo
(74) *Attorney, Agent, or Firm* — Kelley Drye & Warren LLP

(57) ABSTRACT

Devices and methods for detecting drugs, such as gamma hydroxybutyrate and gamma butyrolactone, using infrared spectrometry, and alerting an intended target of the drug, or others, to the presence of the drug.

21 Claims, 3 Drawing Sheets

(56) References Cited

OTHER PUBLICATIONS

"Non-Destructive Determination of Ethanol Levels in Fermented Alcoholic Beverages Using Fourier Transform Mid-nfrared Spectrascopy", Debebe et al, Mar. 24, 2017.
"An Old, Dangerous Drug Has Made a Comeback with a New Generation of Users", S. Richardson, Aug. 13, 2020.
"What is Raman Spectroscopy?", Horiba, Sep. 30, 2021.
"Drug-Facilitated Sexual Assault", C. Sandal, 2020.
"Spectroscopy as a Tool for Detection and Monitoring of Coronavirus (COVID-19", R.S. Khan and I.U. Rehman, 2020.
"GHB Fact Sheet", Department of Justice, Drug Enforcement Agency, Apr. 2020.
"Gamma-butryrolactone (GBL) Critical Review Report", World Health Organization, Jun. 2014.
"Drug-Facilitated Sexual Assault", Drug Enforcement Administration, 2017.
"In-line Monitoring of Alcohol Precipitation by Near-Infrared Spectroscopy in Conjunction with Multivariate Batch Modeling", H. Huang and H. Qu, 2011.
"Near-Infrared Laboratory Spectroscopy of Mineral Chemistry: A Review", F. Van Der Meer, 2017.
"Drink Smart Drink Safe", Date Rape Drug Test Coasters.

\* cited by examiner

METHODS AND APPARATUS FOR DETECTING INCAPACITATING DRUGS

BACKGROUND OF THE INVENTION

Drug Facilitated Sexual Assault is a term used to describe instances of sexual assault where the victim is unable to provide consent due to drug and/or alcohol consumption. As of 2014, nearly 11 million women in the United States were reported to have been raped while drunk, drugged, or high. Oftentimes rape victims have been drugged by ingesting a psychotropic substance that has been added to their drink without their knowledge.

Two drugs that may inhibit a person's ability to consent to sexual conduct and limit their ability to remember an assault are gamma hydroxybutyrate (GHB) and gamma butyrolactone (GBL). GBL is an analogue for GHB. GBL is readily converted to GBH within the body following ingestion. GHB is colorless and odorless and therefore may be conspicuously added to drinks. It causes a person to feel groggy and sleepy and may lead to unconsciousness. When a person recovers from exposure to GHB or GBL, their ability to recall events that occurred during the period of intoxication may be impaired.

Existing techniques for testing for the presence of date rape drugs have significant drawbacks. For example, a product called the "Drink Safe Coaster" offered for sale by Drink Safe Technologies tests the pH of a liquid when a sample of the liquid is applied to the coaster. If the liquid has a pH corresponding to a certain type of drug, the coaster changes color. But when used to test for the presence of a drug, the coaster may generate false positive or false negative indications, depending on the acidity of the solvent (e.g., drink) in which the drug is dissolved. For example, the coaster does not indicate the presence of GBH when it is mixed in an acidic liquid. Also, products that indicate the presence of a date rape drug by changing color may be rendered ineffective if the drink to be tested has a dark color that masks the results of the test.

Spectroscopic techniques involve the investigation and measurement of spectra produced when materials interact with or emit electromagnetic radiation. Infrared spectrometry is the measurement of the interactions between infrared light and matter. When infrared light, typically limited to a particular frequency range, is directed toward a compound, a detector positioned on the opposite side of the compound may be used to identify the frequencies of light that pass through the compound. The frequencies of light that do not pass through the compound, typically represented by dark bands, are absorbed by the compound. Determination of the frequencies of light that are absorbed may be used to identify molecules within the compound, as each molecule has a unique absorption characteristic.

SUMMARY OF THE INVENTION

The present invention is directed to devices and methods for detecting drugs, such as GHB and GBL, using infrared spectrometry. One objective of the present invention is to identify the presence of a date rape drug surreptitiously added to a person's drink, and alert that person to the presence of the drug before they ingest the drink. Another objective of the present invention is to notify others to the presence of the date rape drug surreptitiously added to a person's drink. Notifications may be sent to, for example, the local authorities or an emergency contact for the person who is the target of a date rape drug. Numerous variations may be practiced in the preferred embodiment.

BRIEF DESCRIPTION OF THE DRAWINGS

A further understanding of the invention can be obtained by reference to exemplary embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

DETAILED DESCRIPTION OF THE INVENTION

Figure 1:
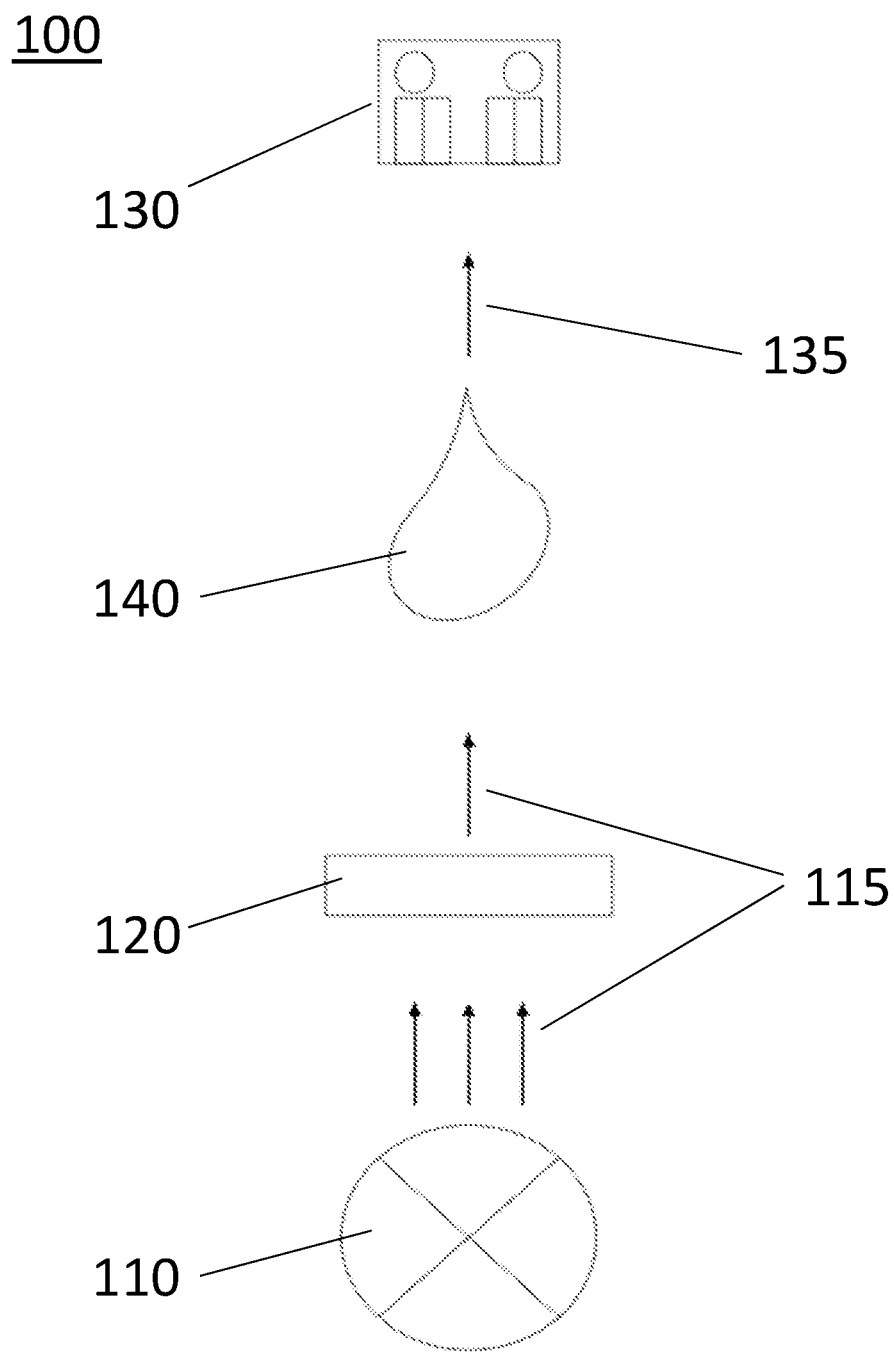
FIG. 1 depicts a device in accordance with the present invention.

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It should also be noted that, as used in the specification and the appended claims, the singular forms "a", "an", and "the" include plural referents unless the context clearly indicates otherwise.

Use of the term "exemplary" means illustrative or by way of example, and any reference herein to "the invention" is not intended to restrict or limit the invention to the exact features or steps of any one or more of the exemplary embodiments disclosed in the present specification. Also, repeated use of the phrase "in one embodiment," "in an exemplary embodiment," or similar phrases do not necessarily refer to the same embodiment, although they may. It is also noted that terms like "preferably," "commonly," and "typically," are not used herein to limit the scope of the claimed invention or to imply that certain features are critical, essential, or even important to the structure or function of the claimed invention. Rather, those terms are merely intended to highlight alternative or additional features that may or may not be used in a particular embodiment of the present invention.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Referring to FIG. 1, there is shown a first embodiment of a detection device (100) in accordance with the present invention. Detection device (100) may include light source (110), filter (120), and detector (130). Light source (110) may be configured to emit infrared radiation (115). The frequency of infrared radiation (115) emitted from light source (110) may have a predetermined value or predetermined range of values. Light source (110) may also be oriented so that infrared radiation (115) is directed toward and passes through filter (120). Filter (120) may be, for example, a spectral filter/IR bandpass filter. Filter (120) may limit the wavelength of infrared radiation (115) so that it is restricted to a particular range. The range may be, for example, 5.5 μm+/−80 nm. Detector (130) may be, for example, a thermopile detector having a window between 190 nm-20 μm.

A sample (140) to be analyzed by detection device (100) may be located between filter (120) and detector (130). Infrared radiation (115) that passes through filter (120) may interact with sample (140). The resulting radiation (135) that is not absorbed by sample (140) may be received by detector (130).

Detection device (100) may further include processor (150), non-transitory memory (160), and/or wireless transceiver (170), not shown. Computer program instructions stored in non-transitory memory (170) may be executed by processor (150) to cause detection device (100) to perform certain operations. For example, the computer program instructions may cause detection device (100) to wirelessly pair with a mobile device (190), not shown, via wireless transceiver (170).

Figure 2:
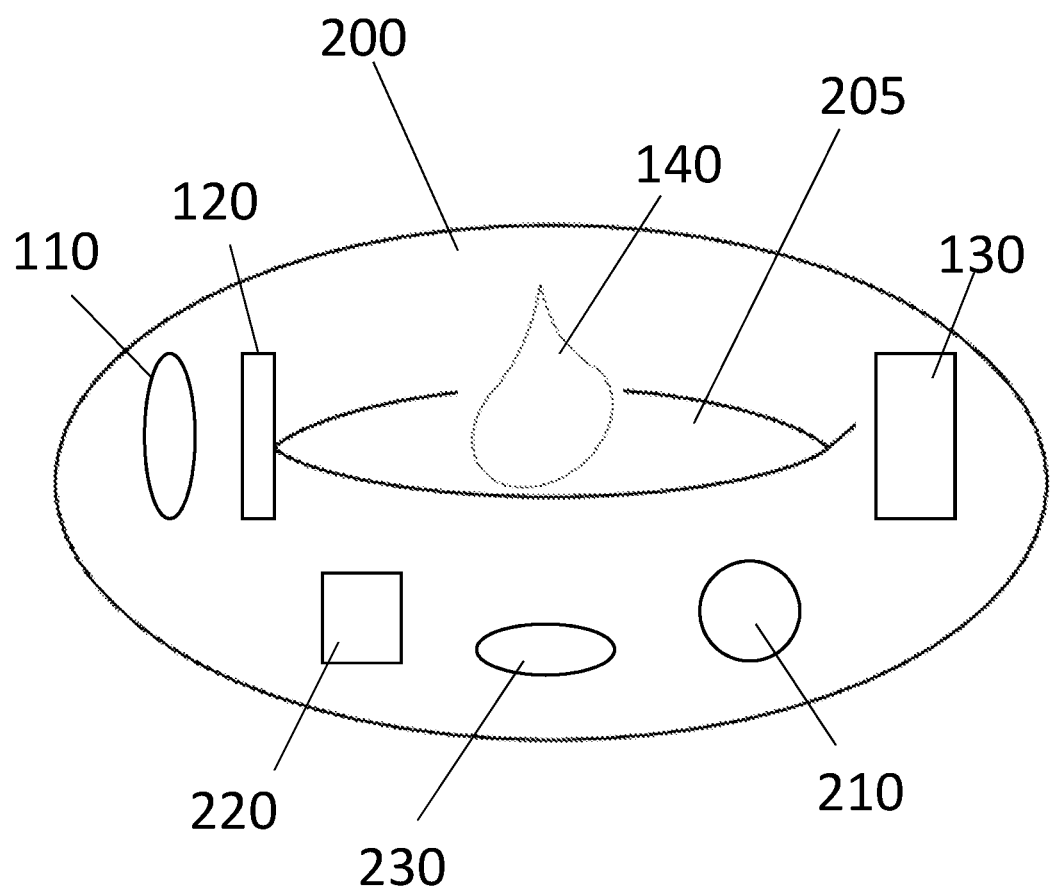
FIG. 2 depicts a device in accordance with the present invention.

The detection device may take various forms, including portable devices such as wearable items. For example, as shown in FIG. 2, detection device (200) may have a toroidal form that may be, for example, worn as a bracelet. Detection device (200) may be placed on a flat surface such as a table, and sample (140) may be placed within the enclosed space (205) surrounded by detection device (200). Detection device (200) may also include one or more components that could be used to alert the user of detection device (200) to the presence of a drug in sample (140). For example, detection device (200) may include a speaker (210), vibration motor (220), and/or warning light (230).

The computer program instructions may cause detection device (100, 200) to generate infrared radiation from light source (110). The computer program instructions may then cause detection device (100, 200) to determine, based on data generated from detector (130), whether such data indicates the presence of a drug, such as GHB or GBL, in sample (140). If the data indicates the presence of the drug in sample (140), the computer program instructions may cause detection device (100, 200) to transmit a signal to mobile device (190) via wireless transceiver (170). Mobile device (190) may be, for example, a mobile phone, a tablet, or a smart watch. Mobile device (190) may have a display, a speaker, a wireless transceiver, and/or one or more physical keys. The signal transmitted to mobile device (190) may cause mobile device (190) to display a message on the mobile device display, emit a sound through the speaker, transmit a message such as a text message, and/or place a telephone call. Mobile device (190) may be configured to send a text message and/or place a telephone call, upon receiving the transmitted signal, using contact information previously stored on mobile device (190) and/or to local authorities.

Additionally or alternatively, if the data generated from detector (130) indicates the presence of a particular drug in sample (140), the computer program instructions may cause detection device (100, 200) to generate an alert that the drug has been detected. The alert may comprise, for example, sound emitted from speaker (210), vibration caused by the vibration motor (220), and/or light emitted by a second light source (230).

Figure 3:
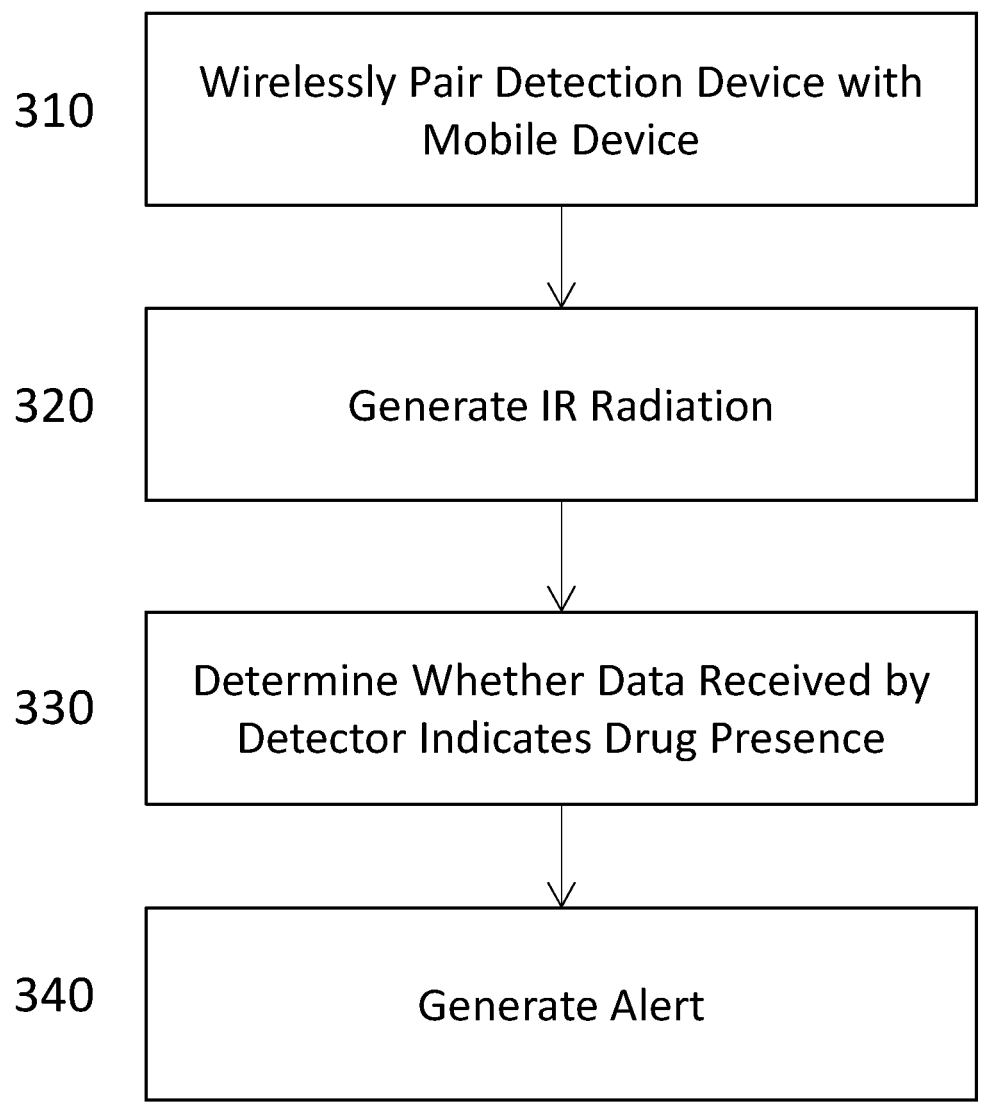
FIG. 3 is a flowchart of a method in accordance with the present invention.

FIG. 3 depicts a flowchart showing a method for detecting a drug such as GHB or GBL in accordance with the present invention. At Step 310, the detection device is wirelessly paired with a mobile device. At Step 320, a light source of the detection device emits infrared radiation that passes through a filter, passes through a sample, and is received by a detector. At Step 330, data from the detector is used to determine whether a drug is present in the sample. At Step 340, the detection device generates an alert indicating the presence of the drug.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A toroidal-shaped portable detection device for detecting a drug in a solution, comprising:
    a filter;
    a light source at a first location of the toroidal shape and configured to emit infrared radiation through the filter and through a space surrounded by the toroidal shape;
    a detector at a second location of the toroidal shape that is diametrically opposite to the first location, said detector configured to receive the infrared radiation emitted by the light source after it passes through the filter and through said space;

a processor;

a wireless transceiver;

a non-transitory memory; and computer program instructions stored in the non-transitory memory which, when executed by the processor, cause the portable detection device to perform operations comprising:

wirelessly pairing the portable detection device with a mobile device via the wireless transceiver;

generating infrared radiation from the light source;

determining, based on data generated from the detector, whether such data indicates the presence of the drug;

upon determining the presence of the drug, transmitting a signal to the mobile device via the wireless transceiver.

2. The portable detection device of claim 1, wherein the drug is gamma hydroxybutyrate.

3. The portable detection device of claim 2, wherein the determination of the presence of the drug is based on the data generated by the detector indicating that, of the infrared radiation generated by the light source, infrared radiation in the range of 790 nm-20 μm has been absorbed.

4. The portable detection device of claim 1, wherein the drug is gamma butyrolactone.

5. The portable detection device of claim 4, wherein the determination of the presence of the drug is based on the data generated by the detector indicating that, of the infrared radiation generated by the light source, infrared radiation in the range of 790 nm-20 μm has been absorbed.

6. The portable detection device of claim 1, wherein the filter inhibits radiation having a wavelength below 1500 and above 2000 from passing through it.

7. The portable detection device of claim 1, wherein the signal transmitted to the mobile device causes the mobile device to display a message.

8. The portable detection device of claim 1, wherein the signal transmitted to the mobile device causes the mobile device to emit a sound.

9. The portable detection device of claim 1, wherein the signal transmitted to the mobile device causes the mobile device to transmit a message to another device.

10. The portable detection device of claim 1, wherein the signal transmitted to the mobile device causes the mobile device to place a telephone call.

11. A toroidal-shaped portable detection device for detecting a drug in a solution, comprising:

a filter;

a light source at a first location of the toroidal shape and configured to emit infrared radiation through the filter and through a space surrounded by the toroidal shape;

a detector at a second location of the toroidal shape that is diametrically opposite to the first location, said detector configured to receive the infrared radiation emitted by the light source after it passes through the filter and through said space;

a processor;

a wireless transceiver;

a non-transitory memory; and computer program instructions stored in the non-transitory memory which, when executed by the processor, cause the portable detection device to perform operations comprising:

wirelessly pairing the portable detection device with a mobile device via the wireless transceiver;

generating infrared radiation from the light source;

determining, based on data generated from the detector, whether such data indicates the presence of the drug;

upon determining the presence of the drug, generating an alert that the drug has been detected.

12. The portable detection device of claim 11, wherein the drug is gamma hydroxybutyrate.

13. The portable detection device of claim 12, wherein the determination of the presence of the drug is based on the data generated by the detector indicating that, of the infrared radiation generated by the light source, infrared radiation in the range of 790 nm-20 μm has been absorbed.

14. The portable detection device of claim 11, wherein the drug is gamma butyrolactone.

15. The portable detection device of claim 14, wherein the determination of the presence of the drug is based on the data generated by the detector indicating that, of the infrared radiation generated by the light source, infrared radiation in the range of 790 nm-20 μm has been absorbed.

16. The portable detection device of claim 11, wherein the filter inhibits radiation having a wavelength below 1500 and above 2000 from passing through it.

17. The portable detection device of claim 11, wherein the portable detection device further comprises a speaker and the alert comprises sound emitted from the speaker.

18. The portable detection device of claim 11, wherein the portable detection device further comprises a vibration motor and the alert comprises vibration caused by the vibration motor.

19. The portable detection device of claim 11, wherein the portable detection device further comprises a warning light and the alert comprises light emitted by the warning light.

20. A portable detection device for detecting a drug in a solution, comprising:

a filter;

a light source configured to emit infrared radiation through the filter;

a detector configured to receive the infrared radiation emitted by the light source after it passes through the filter;

a processor;

a wireless transceiver;

a non-transitory memory; and computer program instructions stored in the non-transitory memory which, when executed by the processor, cause the portable detection device to perform operations comprising:

wirelessly pairing the portable detection device with a mobile device via the wireless transceiver;

generating infrared radiation from the light source;

determining, based on data generated from the detector, whether such data indicates the presence of the drug;

upon determining the presence of the drug, transmitting a signal to the mobile device via the wireless transceiver, wherein the signal transmitted to the mobile device causes the mobile device to transmit a message to another device.

21. A portable detection device for detecting a drug in a solution, comprising:

a filter;

a light source configured to emit infrared radiation through the filter;

a detector configured to receive the infrared radiation emitted by the light source after it passes through the filter;

a processor;

a wireless transceiver;

a non-transitory memory; and computer program instructions stored in the non-transitory memory which, when executed by the processor, cause the portable detection device to perform operations comprising:
- wirelessly pairing the portable detection device with a mobile device via the wireless transceiver;
- generating infrared radiation from the light source;
- determining, based on data generated from the detector, whether such data indicates the presence of the drug;
- upon determining the presence of the drug, transmitting a signal to the mobile device via the wireless transceiver, wherein the signal transmitted to the mobile device causes the mobile device to place a telephone call.

* * * * *